US010677779B2

(12) United States Patent
Shin

(10) Patent No.: US 10,677,779 B2
(45) Date of Patent: Jun. 9, 2020

(54) PLATELET TEST CHIP

(71) Applicant: Korea University Research and Business Foundation, Seoul (KR)

(72) Inventor: Se-Hyun Shin, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 190 days.

(21) Appl. No.: 15/553,284

(22) PCT Filed: Feb. 23, 2016

(86) PCT No.: PCT/KR2016/001730
§ 371 (c)(1),
(2) Date: Aug. 24, 2017

(87) PCT Pub. No.: WO2016/137188
PCT Pub. Date: Sep. 1, 2016

(65) Prior Publication Data
US 2018/0031540 A1 Feb. 1, 2018

(30) Foreign Application Priority Data
Feb. 24, 2015 (KR) .......... 10-2015-0025536

(51) Int. Cl.
*G01N 33/00* (2006.01)
*G01N 33/49* (2006.01)
(Continued)

(52) U.S. Cl.
CPC ..... *G01N 33/4915* (2013.01); *B01F 13/0059* (2013.01); *B01F 13/0818* (2013.01);
(Continued)

(58) Field of Classification Search
CPC ................................ G01N 33/4915
(Continued)

(56) References Cited

U.S. PATENT DOCUMENTS

2007/0196820 A1 * 8/2007 Kapur .............. B01L 3/502746
435/5

FOREIGN PATENT DOCUMENTS

KR 10-1193566 B1 10/2012

OTHER PUBLICATIONS

Minamoto et al. "Detection of Platelet Adhesion/ Aggregation to Immobmzed ligands on Microbeads by an Aggregometer" Thrombosis and Haemostasis, 1996, vol. 76, No. 6, pp. 1072-1079 (Year: 1996).*

(Continued)

*Primary Examiner* — Christopher Adam Hixson
*Assistant Examiner* — Emily R. Berkeley
(74) *Attorney, Agent, or Firm* — NSIP Law

(57) ABSTRACT

Disclosed is a platelet-testing chip. The platelet-testing chip includes a plurality of sample chambers storing blood samples, stirrers provided in the sample chambers to apply shearing force to the blood samples, a plurality of waste sample chambers provided so as to correspond to the plurality of the sample chambers, microchannels, through which the sample chambers and the waste sample chambers corresponding to each other are independently connected to thus form paths through which the blood samples flow from the sample chambers to the corresponding waste sample chambers, and microbeads which are received in one or more of the plurality of the sample chambers and which are coated with a reagent for activating platelets on an outer surface thereof. When the blood samples are transferred from the sample chambers through the microchannels, the microbeads are transferred together with the blood samples.

11 Claims, 9 Drawing Sheets

(51) Int. Cl.
    *B01F 13/08*   (2006.01)
    *B01F 13/00*   (2006.01)
    *B01L 3/00*    (2006.01)

(52) U.S. Cl.
    CPC .... *B01L 3/502761* (2013.01); *G01N 33/4905* (2013.01); *B01L 2200/0668* (2013.01); *B01L 2300/0816* (2013.01); *B01L 2300/0864* (2013.01); *B01L 2300/0867* (2013.01); *B01L 2300/0883* (2013.01); *B01L 2400/043* (2013.01); *B01L 2400/049* (2013.01)

(58) Field of Classification Search
    USPC .................................................... 422/502
    See application file for complete search history.

(56) References Cited

OTHER PUBLICATIONS

Cook, Bernard C., "Reactivity of Human platelets with Immobilized Fibrinogen is Dictated by the Chemical Character of the Surface." Thrombosis Research vol. 104, 2001, pp. 39-48.

Song, Suk-Heung, et al. "Migration distance-based platelet function analysis in a microfluidic system," Biomicrofluidics, (vol. 7, No. 6 (10 pages in English).

International Search Report dated Jul. 25, 2016 in Corresponding Korean Patent Application No. PCT/KR2016/001730 (2 pages in English and 2 pages in Korean).

* cited by examiner

PLATELET TEST CHIP

CROSS REFERENCE TO RELATED APPLICATIONS

This application is a National Phase entry of PCT Application No. PCT/KR2016/001730, filed on Feb. 23, 2016, which claims priority under 35 U.S.C. § 119(e), 120 and 365(c) to Korean Patent Application No. 10-2015-0025536, filed on Feb. 24, 2015.

TECHNICAL FIELD

The present invention relates to a platelet-testing chip. More particularly, the present invention relates to a platelet-testing chip for testing the characteristics of platelets in a blood sample of a subject using a flow path design of a microchannel regardless of the viscosity and the hematocrit value of the blood sample or the function and the value of a vWF thereof.

BACKGROUND ART

Platelet function tests are widely used as congenital platelet function abnormality or pre-operative screening tests, and are particularly important for differentiating hemorrhagic diseases caused by congenital or acquired platelet function abnormalities among hemorrhagic diseases having no platelet numerical abnormalities.

Recently, such platelet function tests have come to be widely used to test for increased hemorrhagic tendency as an effect of an anti-platelet drug, which is used for the treatment and prevention of cardiovascular diseases, or to test for resistance to a drug.

A bleeding time (BT) test is a bleeding-time measurement test that was developed about 100 years ago and has been used as a platelet function screening test to date. However, there are problems in that the platelet function test currently in use is difficult to standardize, has low clinical usefulness, and requires the use of an invasive method. Accordingly, an objective measurement method for measuring the platelet function is required.

In the case of a platelet function analyzer (e.g.: PFA-100), which is designed to solve the above-described problems and which is used as a technique for measuring the platelet function, in order to measure the characteristic of aggregation of platelets caused by a von Willebrand factor (vWF) activated at a high shear rate, the clogging time that is required for clogging of orifice holes of an orifice, which is coated with collagen, adenosine diphosphate (ADP), or epinephrine, due to aggregation of platelets after enabling whole blood to flow through a long capillary at a high shear rate is measured using a pressure or a flow rate.

In order to perform the platelet function test, it is inevitable to depend on the function of the vWF, the test is dependent on the hematocrit (Hct), and the anti-aspirin or anti-clopidogrel test cannot be performed, which are considered to be drawbacks. Further, there is a drawback in that testing costs are increased due to the necessity of a two-stage test process for the platelet function test.

In particular, blood samples must be exposed at a high shear rate for a predetermined period of time or longer in order to activate the vWF. For this purpose, PFA-100 adopts a method of enabling blood to rapidly flow through a very long capillary. However, this method has problems in that a large amount of blood is required and that the vWF located at the center of the tube, at which the shear rate is a minimum, is not activated even though the vWF located near the capillary wall, at which the shear rate is a maximum, is easily activated. This may cause a problem in the repeatability of the test result.

In order to solve the above-described problems, Korean Patent Registration No. 10-1193566 proposes a micro-chip-based platelet multifunction testing device. The device includes a sample storage chamber in which a blood sample is received, a stirrer provided in the sample storage chamber to induce a shear flow in the blood sample, parallel channels provided to form a plurality of paths through which the blood stirred using the stirrer flows, a vacuum device connected to the ends of the parallel channels to enable the stirred blood to flow through the parallel channels while maintaining a constant pressure, a light source provided at the rear end of the parallel channels to radiate light to the parallel channels, and an image sensor which receives the light transmitted through the blood in the parallel channels and which converts the light into an electrical signal, thus measuring the flow rate of blood. Accordingly, it is possible to test a plurality of platelet functions by a single test, and an effect of not only reducing the test time but also reducing the testing costs is provided.

However, in the case of the micro-chip-based platelet multifunction testing device, basically, the blood sample is stirred in one sample storage chamber and made to flow through a plurality of parallel channels, and the absolute flow distance of the blood is measured, thereby testing the function of the platelets. Accordingly, the problem of variation in the flow distance of the blood depending on the viscosity or the size of the hematocrit of the blood of a subject, regardless of activation of the platelets, has not yet been solved. Further, the problem of absolute dependency on the function of the vWF has not yet been solved, and there is a drawback in that a drug reaction test for anti-platelet agents cannot be performed.

For example, when the blood of a subject has a high viscosity, the flow distance of the blood flowing through the parallel channels may be shortened, and this phenomenon may lead to errors in judging the platelets to be activated.

Therefore, there is a demand for developing a novel testing chip, testing device, and testing method which can remove, from the test, the undesired influence of the viscosity, the hematocrit, or the vWF of the blood on a technology in which the transfer distance of the blood is judged using the extent of activation of platelets due to the shearing force or the extent of reaction of the platelets according to the anti-platelet agent.

DISCLOSURE

Technical Problem

Accordingly, the present invention has been made keeping in mind the above problems occurring in the related art, and an object of the present invention is to provide a platelet-testing chip for testing the characteristics of platelets in a blood sample of a subject using a flow path design of a microchannel regardless of the viscosity and the hematocrit value of the blood sample or the function and the value of a vWF thereof, and a platelet-testing device using the same.

The technical problems to be solved by the present invention are not limited to the above-mentioned technical problems. Other technical subjects not mentioned can be clearly understood from the following description by a person having ordinary skill in the art to which the present invention belongs.

Technical Solution

In order to accomplish the above object, the present invention provides a platelet-testing chip including: a plurality of sample chambers storing blood samples, stirrers provided in the sample chambers to stir the blood samples, a plurality of waste sample chambers provided so as to correspond to the plurality of the sample chambers, microchannels, through which the sample chambers and the waste sample chambers corresponding to each other are independently connected to thus form paths through which the blood samples flow from the sample chambers to the corresponding waste sample chambers, one or more clogging-induction channel units formed on the paths of the microchannels, and microbeads which are received in one or more of the plurality of the sample chambers and which are coated with a reagent for activating platelets on an outer surface thereof. When the blood samples are transferred from the sample chambers through the microchannels, the microbeads are transferred together with the blood samples, thus inducing clogging of the clogging-induction channel units with the blood samples.

The platelets of the blood samples may be attached to the microbeads and are aggregated in the sample chambers and the microchannels, and may then flow into the clogging-induction channel units, thus clogging the clogging-induction channel units.

Further, a reagent for activating the platelets may be applied on inner wall surfaces of the clogging-induction channel units to induce clogging.

In addition, the reagent applied on the inner wall surfaces of the clogging-induction channel units may be any one among agonists including collagen, fibrinogen, adenosine diphosphate (ADP), epinephrine, arachidonic acid, thromboxane A2, thrombin, and iso-thrombin-receptor-activating peptide (iso-TRAP), or a combination thereof.

Further, inner diameters of the clogging-induction channel units may be smaller than inner diameters of the microchannels in order to induce clogging.

In addition, the platelet-testing chip may further include magnetic units applying a magnetic field to the clogging-induction channel units. The microbeads may include a material having magnetism or a magnetizable material so as to be captured in the clogging-induction channel units due to the magnetism of the magnetic units while flowing together with the blood samples, thus impeding or stopping the flow of the blood samples.

In addition, a reagent applied on the microbeads may be any one among agonists including collagen, fibrinogen, adenosine diphosphate (ADP), epinephrine, arachidonic acid, thromboxane A2, thrombin, and iso-thrombin-receptor-activating peptide (iso-TRAP), or a combination thereof.

A plurality of the sample chambers may include a standard sample chamber and one or more control sample chambers, and one or more of final reaching distances, reaching times required for the final reaching distances, and flow rates of the blood samples, which flow from the standard sample chamber to the corresponding microchannel, and the blood samples, which flow from the control sample chambers to the corresponding microchannels, may be selected, followed by comparison of the same, thus measuring the characteristics of the platelets.

In addition, the platelet-testing chip may further include an stirring controller individually controlling stirrers provided in the sample chambers so that magnitudes of shearing forces applied to the blood samples in the sample chambers are individually controlled.

In addition, the stirring controller may control the stirrers in standard sample chambers so that the shearing forces having magnitudes insufficient to activate platelets are applied to the blood samples in the standard sample chambers, and may also control the stirrers in control sample chambers so that shearing forces having magnitudes sufficient to activate the platelets are applied to the blood samples in the control sample chambers, and microbeads received in the standard sample chambers and the control sample chambers may be coated with the same reagent so that an extent of reaction of the platelets depending on the shearing forces is identified.

Further, control sample chambers may be provided in a plural number, the stirring controller may control the stirrers in standard sample chambers so that shearing forces having magnitudes insufficient to activate platelets are applied to the blood samples in the standard sample chambers, and may also control the stirrers in the control sample chambers so that the shearing forces having different magnitudes sufficient to activate the platelets are applied to the blood samples in the control sample chambers in order to determine the extent of activation of the platelets depending on the magnitudes of the shearing forces, and microbeads received in the standard sample chambers and the control sample chambers may be coated with the same reagent so that an extent of reaction of the platelets depending on the shearing forces is identified.

Control sample chambers may be provided in a plural number, microbeads may be received only in the control sample chambers, the microbeads received in the control sample chambers may be coated with different reagents, and the stirring controller may apply shearing forces having magnitudes insufficient to activate platelets to the blood samples in the standard sample chambers and the control sample chambers.

In addition, the platelet-testing chip may further include addition chambers which are formed between the clogging-induction channel units and the sample chambers and into which calcium ions or adenosine diphosphates (ADP) are provided. The calcium ions or the adenosine diphosphates (ADP) may be transferred together with the blood samples passing through the addition chambers, thus promoting the activation of the platelets using a reagent.

In order to accomplish the above object, the present invention also provides a platelet-testing chip including: a plurality of sample chambers storing blood samples, stirrers provided in the sample chambers to stir the blood samples, a plurality of waste sample chambers provided so as to correspond to the plurality of the sample chambers, microchannels, through which the sample chambers and the waste sample chambers corresponding to each other are independently connected to thus form paths through which the blood samples flow from the sample chambers to the corresponding waste sample chambers, one or more clogging-induction channel units which are formed at a front portion of the microchannels and which have a flow area that is larger than a flow area of the microchannels, magnetic units applying a magnetic field to the clogging-induction channel units, and microbeads including a material having magnetism or a magnetizable material, which are received in one or more of a plurality of the clogging-induction channel units and which are coated with a reagent for activating platelets on an outer surface thereof. The platelets in the blood samples passing through the clogging-induction channel units are activated by the reagent, thus inducing attachment of the platelets to the microbeads and aggregation of the platelets, and the microbeads are captured in the clogging-induction channel units due to the magnetic field of the magnetic units, thus inducing clogging with the blood samples.

The plurality of the sample chambers may include a standard sample chamber and at least one control sample chamber, the plurality of clogging-induction channel units may include a standard clogging-induction channel unit connected to the standard sample chamber and a control clogging-induction channel unit connected to the control sample chamber, and one or more of final reaching distances, reaching times required for the final reaching distances, and flow rates of the blood samples that flow from the standard sample chamber to the corresponding microchannel and the blood samples that flow from the control sample chamber to the corresponding microchannel may be selected, followed by comparison thereof, thus measuring the characteristics of the platelets.

Further, the platelet-testing chip may further include an stirring controller individually controlling stirrers provided in the sample chambers so that magnitudes of shearing forces applied to the blood samples in the sample chambers are individually controlled.

In addition, the stirring controller may control the stirrers in standard sample chambers so that the shearing forces having magnitudes insufficient to activate platelets are applied to the blood samples in the standard sample chambers, and may also control the stirrers in control sample chambers so that the shearing forces having magnitudes sufficient to activate the platelets are applied to the blood samples in the control sample chambers, and microbeads received in the standard sample chambers and the control sample chambers may be coated with the same reagent so that the extent of reaction of the platelets depending on the shearing forces is identified.

In addition, control sample chambers may be provided in a plural number, the stirring controller may control the stirrers in standard sample chambers so that shearing forces having magnitudes insufficient to activate platelets are applied to the blood samples in the standard sample chambers, and may also control the stirrers in the control sample chambers so that shearing forces, having different magnitudes sufficient to activate the platelets, are applied to the blood samples in the control sample chambers in order to determine the extent of activation of the platelets depending on the magnitudes of the shearing forces, and microbeads received in standard clogging-induction channel units and control clogging-induction channel units may be coated with the same reagent so that the extent of reaction of the platelets depending on the shearing forces is identified.

Control sample chambers may be provided in a plural number, microbeads may be received only in control clogging-induction channel units, the microbeads received in the control clogging-induction channel units may be coated with different reagents, and the stirring controller may apply the shearing forces having magnitudes insufficient to activate platelets to the blood samples in the standard sample chambers and control sample chambers.

In addition, the microbeads may be provided depending on the density and the size of red blood cells.

Further, the microbeads may be formed so as to have a size between the size of the platelets and the size of white blood cells.

In addition, the microbeads may have a plurality of pores, through which an inner part communicates with an outer part, and may be coated with the reagent so that the reagent flows into the pores.

In order to accomplish the above object, the present invention also provides a platelet-testing chip including: a plurality of sample chambers storing blood samples, stirrers provided in the sample chambers to stir the blood samples, a plurality of waste sample chambers provided so as to correspond to the plurality of the sample chambers, microchannels, through which the sample chambers and the waste sample chambers corresponding to each other are independently connected to thus form paths through which the blood samples flow from the sample chambers to the corresponding waste sample chambers, one or more clogging-induction channel units formed on the paths of the microchannels, and microbeads which are received in one or more of the plurality of the sample chambers and which are coated with an antagonist reagent on an outer surface thereof. When the blood samples are transferred from the sample chambers through the microchannels, the microbeads are transferred together with the blood samples, thus inducing clogging of the clogging-induction channel units with the blood samples.

The plurality of the sample chambers may include a standard sample chamber and at least one control sample chamber, the microbeads may be received only in the control sample chamber, and one or more of final reaching distances, reaching times required for the final reaching distances, and flow rates of the blood samples flowing from the standard sample chamber to the corresponding microchannel and the blood samples flowing from the control sample chamber to the corresponding microchannel may be selected, followed by comparison thereof, thus measuring the characteristics of platelets.

In order to accomplish the above object, the present invention also provides a platelet-testing chip including: a plurality of sample chambers in which blood samples are received, one exit chamber spaced apart from the plurality of the sample chambers, and microchannels through which the sample chambers are independently connected to the exit chamber. The blood samples received in the sample chambers simultaneously flow from the sample chambers through the corresponding microchannels due to the vacuum pressure applied through the one exit chamber.

The platelet-testing chip may further include stirrers, provided in the sample chambers to stir the blood samples, and an stirring controller individually controlling the stirrers provided in the sample chambers so that magnitudes of shearing forces applied to the blood samples in the sample chambers are individually controlled.

Further, the platelet-testing chip may include a plurality of waste sample chambers provided so as to correspond to the plurality of the sample chambers, thus connecting the microchannels and the exit chamber, one or more clogging-induction channel units formed on paths of the microchannels, and microbeads which are received in one or more of the plurality of the sample chambers and which are coated with a reagent for activating platelets on an outer surface thereof. When the blood samples are transferred from the sample chambers through the microchannels, the microbeads may be transferred together with the blood samples, thus inducing clogging of the clogging-induction channel units with the blood samples.

Advantageous Effects

According to the present invention having the above-described constitution, blood samples which contain the same blood and which are stirred at different shear rates flow through microchannels, followed by comparison thereof. Thereby, measurement errors occurring depending on the viscosity and the hematocrit value of the blood sample of a subject or variation in the function of a vWF thereof may be eliminated.

Further, various measurements for a flow distance, a flow time, a maximum reaching distance, etc. of the blood sample may be performed in combination using a single test, thereby providing an effect not only of reducing the test time but also of reducing testing costs.

Further, aggregation and attachment of platelets may be very effectively induced using only a small amount of microbeads (less than 1% in hematocrit), whereby the transferring distance and time of blood are largely shortened, thus dramatically reducing the time required for detection.

Further, the vacuum pressure that induces the flow of the blood sample in each microchannel is applied to each microchannel through one exit chamber. Accordingly, the vacuum pressure applied to each microchannel is maintained uniform, and the flows of the blood samples are taken at the same point in time using an image acquisition device such as a camera, whereby it is possible to more accurately test the platelet characteristics.

BEST MODE

The present invention relates to a platelet-testing chip. The platelet-testing chip includes a plurality of sample chambers storing blood samples, stirrers provided in the sample chambers to stir the blood samples, a plurality of waste sample chambers provided so as to correspond to the plurality of the sample chambers, microchannels, through which the sample chambers and the waste sample chambers corresponding to each other are independently connected to thus form paths through which the blood samples flow from the sample chambers to the corresponding waste sample chambers, one or more clogging-induction channel units formed on the paths of the microchannels, and microbeads which are received in one or more of the plurality of the sample chambers and which are coated with a reagent for activating platelets on an outer surface thereof. When the blood samples are transferred from the sample chambers through the microchannels, the microbeads are transferred together with the blood samples, thus inducing clogging of the clogging-induction channel units with the blood samples.

MODE FOR INVENTION

Hereinafter, embodiments of the present invention will be described in detail with reference to the accompanying drawings.

Figure 1:
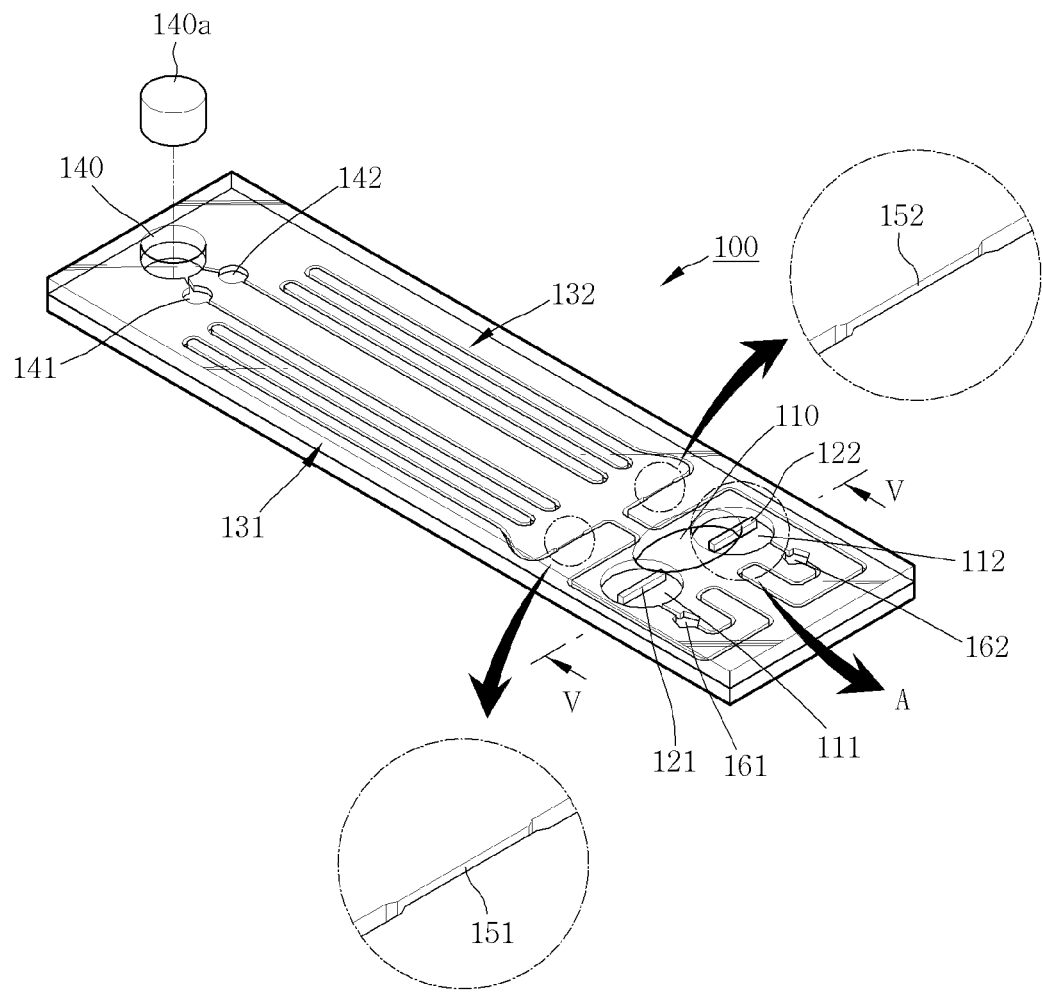
FIG. 1 is a perspective view of a platelet-testing chip according to the present invention.
Figure 2:
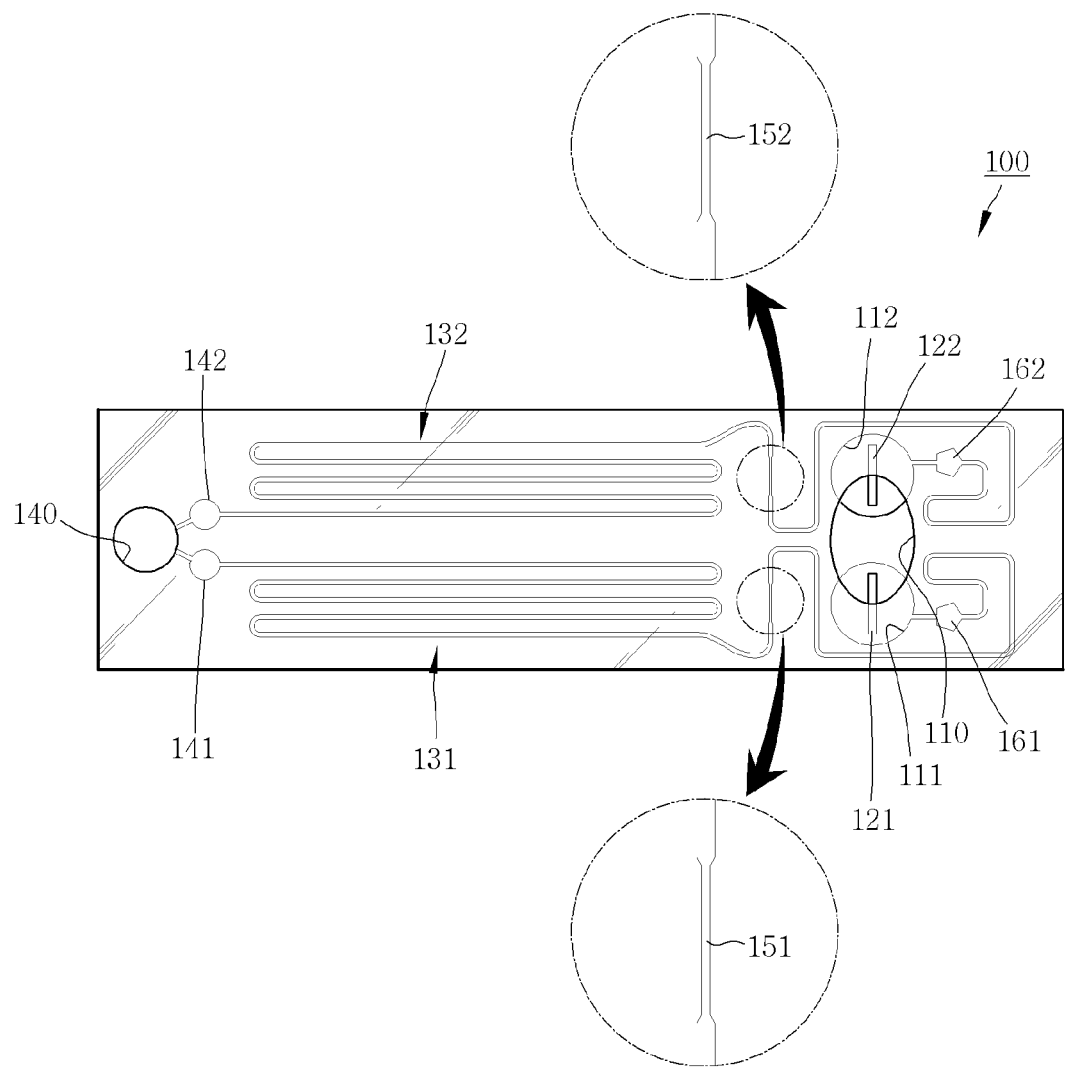
FIG. 2 is a plan view of the platelet-testing chip according to the present invention.
Figure 3:
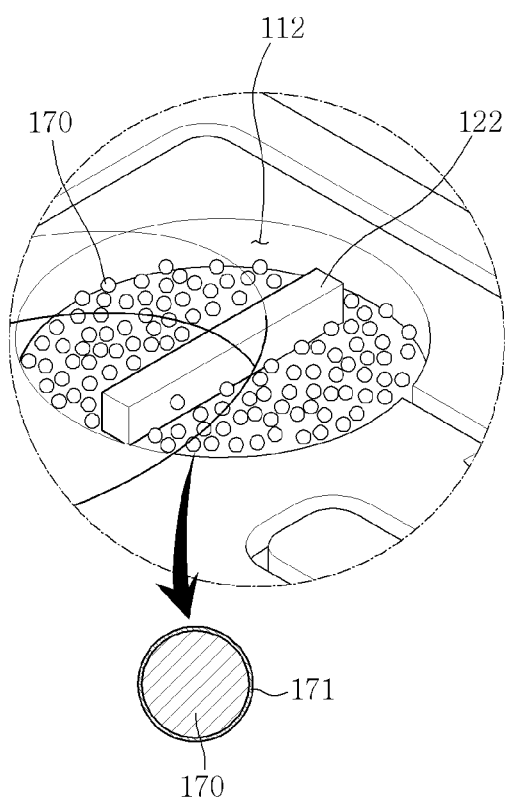
FIG. 3 is an enlarged view of region A in FIG. 1.

FIG. 1 is a perspective view of a platelet-testing chip 100 according to a first embodiment of the present invention, FIG. 2 is a plan view of the platelet-testing chip 100 according to the first embodiment of the present invention, and FIG. 3 is an enlarged view of region A in FIG. 1. Referring to FIGS. 1 to 3, a platelet-testing chip 100 according to a first embodiment of the present invention includes a plurality of sample chambers 111 and 112, microchannels 131 and 132, and an exit chamber 140. Further, the platelet-testing chip 100 according to the first embodiment of the present invention may include stirrers 121 and 122, a plurality of waste sample chambers 141 and 142, clogging-induction channel units 151 and 152, and microbeads 170.

Blood samples are stored in the plurality of sample chambers 111 and 112. The sample chambers 111 and 112 have a substantially circular shape as an example, as shown in FIGS. 1 and 2, but it is readily apparent that the shape of the sample chambers is not limited thereto. The size of the sample chambers 111 and 112 may vary depending on the purpose of use, and the sample chambers may include an optically transparent material so that the inside of the sample chambers is easily observed from the outside.

Figure 4:
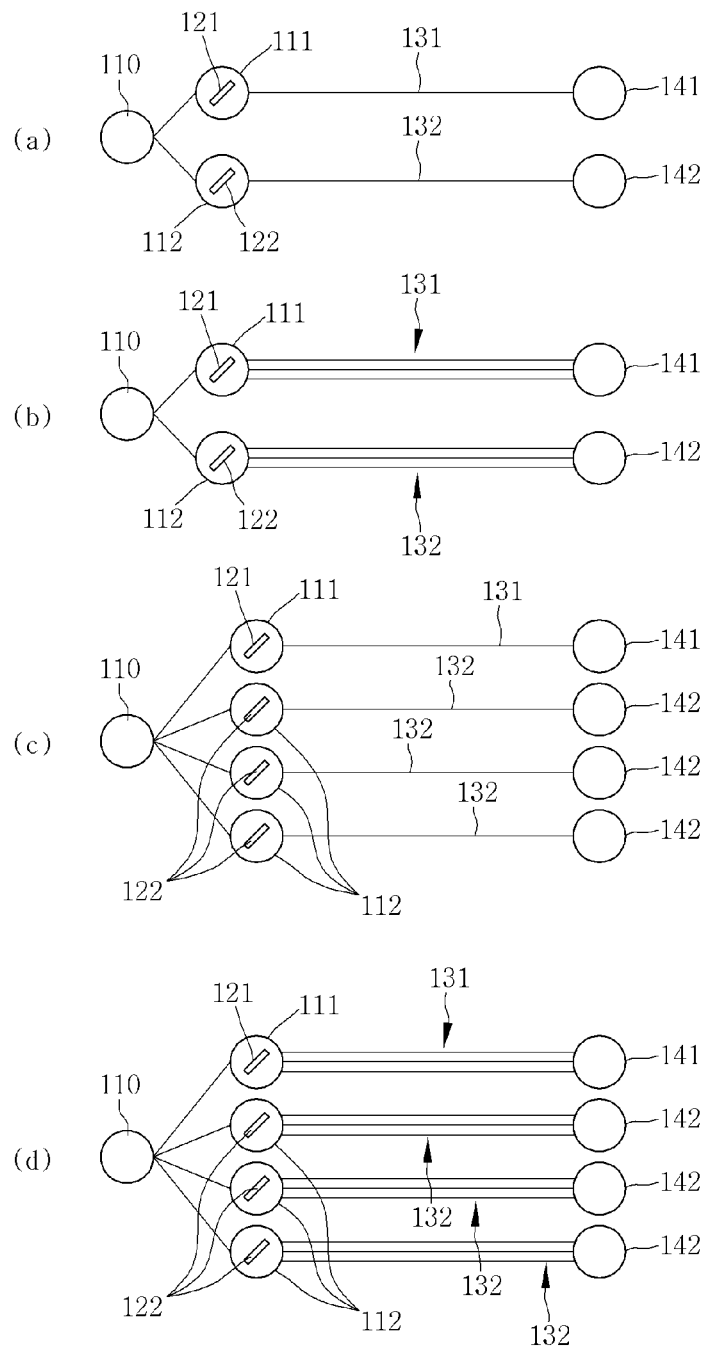
FIG. 4 is a view showing a platelet-testing chip according to another embodiment of the present invention.

In the present invention, the two sample chambers 111 and 112 are shown in FIGS. 1 and 2 by way of example, but it is readily apparent that the number of sample chambers may be three or more. FIG. 4 is a view showing a platelet-testing chip according to another embodiment of the present invention. FIG. 4 shows that the number of sample chambers 111 and 122 and the number of waste sample chambers 141 and 142 may vary, and that the number of microchannels 131 and 132 through which the sample chambers 111 and 122 and the waste sample chambers 141 and 142 are connected, respectively, may also vary.

The plurality of waste sample chambers 141 and 142 is provided corresponding in number to the number of sample chambers 111 and 112. That is, when two sample chambers 111 and 112 are formed, as in the embodiment shown in FIGS. 1 and 2, the two waste sample chambers 141 and 142 are provided to correspond thereto. The waste sample chambers 141 and 142 are provided, by way of example, in a substantially circular shape, like the sample chambers 111 and 112.

The sample chambers 111 and 112 and the waste sample chambers 141 and 142 corresponding to each other are independently connected through the microchannels 131 and 132, respectively. Accordingly, the blood samples received in the sample chambers 111 and 112 flow independently through the microchannels 131 and 132 to the waste sample chambers 141 and 142, respectively. Therefore, the microchannels 131 and 132 form paths, through which the blood samples in the sample chambers 111 and 112 flow to the waste sample chambers 131 and 132, respectively.

FIGS. 1 and 2 exemplifies that the microchannels 131 and 132 are provided in a zigzag arrangement. However, the microchannels may be provided in various shapes, such as a linear shape, a curved shape, or a combination thereof.

Meanwhile, the stirrers 121 and 122 are provided in the sample chambers 111 and 112, respectively. The stirrers 121 and 122 serve to mix the blood samples, received in the sample chambers 111 and 112, with the microbeads 170 or to apply shearing force to the blood samples. In the present invention, for example, the stirrers 121 and 122 are rotatably provided in the sample chambers 111 and 112 so as to rotate according to the control of an stirring controller 160 (see FIG. 5), as will be described later.

Figure 5:
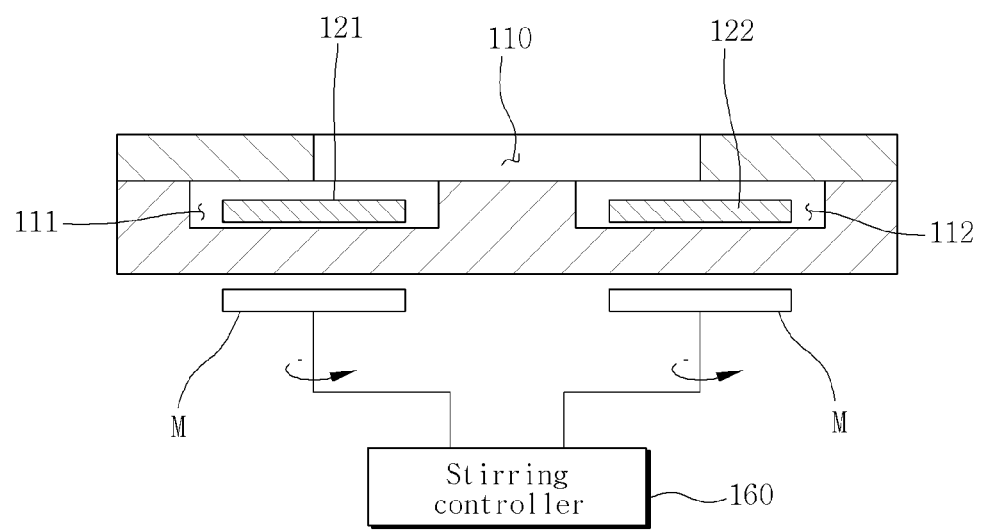
FIG. 5 is a cross-sectional view taken along the line V-V in FIG. 1.

FIG. 5 is a cross-sectional view taken along the line V-V in FIG. 1, and shows an example of the configuration of the stirrers 121 and 122 and the stirring controller 160 according to the first embodiment of the present invention. Referring to FIG. 5, the stirring controller 160 controls the operation of the stirrers 121 and 122. In the present invention, the stirring controller 160 is provided so as to individually control the stirrers 121 and 122. That is, when the stirrers 121 and 122 are rotatably provided in the sample chambers 111 and 112, the stirring controller 160 controls the rotation speeds of the stirrers 121 and 122 so as to be different from each other, thereby making the magnitudes of the shearing forces applied to the blood samples received in the sample chambers 111 and 112 different from each other. Accordingly, the magnitudes of the shearing forces applied to the blood samples in the sample chambers 111 and 112 are made different from each other, thus controlling whether or not the platelets in each blood sample are activated or the extent of activation of the platelets in each blood sample.

In the present invention, for example, the stirring controller 160 enables the stirrers 121 and 122 to rotate using a non-contact method such as magnetic force. Referring to FIG. 5, more specifically, a magnet M may be rotatably provided outside the lower part of the sample chambers 111 and 112, and the stirring controller 160 may control the rotation of the magnet M, thereby controlling the rotation of the stirrers 121 and 122 in the sample chambers 111 and 112.

Meanwhile, the clogging-induction channel units 151 and 152 may be formed on the paths of the microchannels 131 and 132, respectively, and may be formed at the front portions of the microchannels 131 and 132, respectively. FIGS. 1 and 2 shows an example in which one clogging-induction channel unit 151 and 152 is formed in one microchannel 131 and 132, but it is readily apparent that the number of clogging-induction channel units is not limited thereto.

In the present invention, FIGS. 1 and 2 exemplify that the inner diameter of the clogging-induction channel units 151 and 152 is smaller than the inner diameter of the microchannels 131 and 132, thereby inducing clogging of the blood samples.

Further, the inner wall surface of the clogging-induction channel units 151 and 152 may be coated with a reagent for activating the platelets, thus inducing clogging of the blood samples. Examples the reagent for activating the platelets may include any one among agonists such as collagen, fibrinogen, adenosine diphosphate (ADP), epinephrine, arachidonic acid, thromboxane A2, thrombin, and iso-thrombin-receptor-activating peptide (iso-TRAP), or a combination thereof.

Meanwhile, as shown in FIG. 3, the microbeads 170 are received in at least one of the plurality of sample chambers 111 and 112. As shown in the enlarged region of the cross-sectional view of FIG. 3, the outer surface of the microbeads 170 is coated with a reagent 171 for activating the platelets. Examples of the reagent 171 applied on the microbeads 170 according to the first embodiment of the present invention may include any one among agonists such as collagen, fibrinogen, adenosine diphosphate (ADP), epinephrine, arachidonic acid, thromboxane A2, thrombin, and iso-thrombin-receptor-activating peptide (iso-TRAP), or a combination thereof.

Further, the size of the microbeads 170 depends on the size and density of red blood cells. For example, in the case of the size, the microbeads 170 are formed so as to have a size between the size of the platelets and the size of white blood cells. Further, the total amount of the reagent 171 applied on the microbeads 170 may be determined within a range that does not affect a change in physical properties of the blood samples. For example, the total amount may be determined within a range of 2% or less based on the hematocrit.

Therefore, when the blood samples received in the sample chambers 111 and 112 are transferred through the microchannels 131 and 132, the microbeads 170 are transferred together with the blood samples. The reagent 171 applied on the microbeads 170 acts in the sample chambers 111 and 112, which activates the platelets in the blood samples.

That is, the platelets in the blood samples are mixed with the microbeads 170 due to the rotation of the stirrers 121 and 122, and are activated due to the reagent 171 applied on the surface of the microbeads 170, causing attachment and aggregation between the microbeads 170 and the platelets or between the platelets.

Accordingly, the blood samples in the sample chambers 111 and 112 flow through the microchannels 131 and 132 while being mixed with the microbeads 170 coated with the reagent 171 due to the rotation of the stirrers 121 and 122.

The reagent 171 applied on the microbeads 170 is dissolved in the blood samples to activate the platelets contained in the blood samples. The activated platelets become attached to the microbeads, aggregate, and flow through the microchannels 131 and 132. The clogging of the clogging-induction channel units 151 and 152 with the blood samples is induced due to the reagent or the narrow path, which finally clogs the clogging-induction channel units 151 and 152.

When the clogging-induction channel units 151 and 152 are clogged, the flow of the blood samples is stopped, and the characteristics of the platelets may be analyzed using final reaching distances, reaching times required for the final reaching distances, and flow rates of the blood samples, which flow until the clogging-induction channel units 151 and 152 are clogged.

Hereinafter, any one of the sample chambers 111 and 112 is defined as a standard sample chamber 111, and the other is defined as a control sample chamber 112. The embodiment shown in FIGS. 1 and 2 exemplifies the case in which two sample chambers 111 and 112 are provided, with either one of the sample chambers serving as the standard sample chamber 111 and the other serving as the control sample chamber 112. However, when three or more sample chambers 111 and 112 are provided, one or more standard sample chambers 111 may be provided, and at least one of the sample chambers 111 and 112 may serve as the control sample chamber 112.

In the present invention, one or more of final reaching distances, reaching times required for the final reaching distances, and flow rates of the blood samples that flow from the standard sample chamber 111 to the corresponding microchannel 131 and the blood samples that flow from the control sample chamber 112 to the corresponding microchannel 132 are compared to each other, thus measuring the characteristics of the platelets.

Hereinafter, an example of the platelet characteristic test using the platelet-testing chip 100 according to the present invention will be described in detail.

For example, the stirring controller 160 may control the corresponding stirrers 121 and 122 so that different shearing forces are applied to the blood sample received in the standard sample chamber 111 and the blood sample received in the control sample chamber 112. The microbeads 170 received in the standard sample chamber 111 and the control sample chamber 112 are coated with the same reagent so that the extent of reaction of the platelets depending on the shearing force is identified.

More specifically, the stirring controller 160 may control the stirrer 121 in the standard sample chamber 111 so that the shearing force having a magnitude insufficient to activate the platelets is applied to the blood sample in the standard sample chamber 111, and may also control the stirrer 122 in the control sample chamber 112 so that a shearing force having a magnitude sufficient to activate the platelets is applied to the blood sample in the control sample chamber 112. For example, the stirring controller 160 may control the respective stirrers 121 and 122 so that a shearing force of 0.5 Pa or less is applied to the inside of the standard sample chamber 111 and so that a shearing force of 8 Pa or more is applied to the inside of the control sample chamber 112.

The stirring controller 160 may control the stirrers 121 and 122 so as to homogeneously apply the shearing force to all the platelets for a satisfactory time when the shearing force having a magnitude sufficient to activate the platelets is applied, that is, when the shearing force is applied to the control sample chamber 112. In the present invention, for example, the stirring controller 160 enables the stirrers 121 and 122 in the control sample chamber 112 to rotate for any one period of time selected from between 10 seconds and 300 seconds.

Due to the individual control of the stirrers 121 and 122, the platelets of the blood sample in the standard sample chamber 111 flow through the microchannels 131 and 132 in an inactive state, and the platelets of the blood sample in the control sample chamber 112 flow through the microchannels 131 and 132 in an active state.

Therefore, when the blood sample flowing from the control sample chamber 112 to the corresponding microchannel 131 is compared to the blood sample flowing from the standard sample chamber 111 to the corresponding microchannels 131 and 132, the final reaching distances, the reaching times required for the final reaching distances, and the flow rates of the blood samples vary depending on the attachment or aggregation of the activated platelets, and are compared to each other, thereby measuring the degree of shear-induced activation of the blood samples and the extent of aggregation and attachment of the platelets.

Accordingly, different shearing forces may be applied to the same blood sample so as to subject the same blood sample to different shear rates. The characteristics of the platelets may be tested by comparing the shear rates, thereby removing measurement errors that occur due to the absolute value of the transferring distance or rate of the blood sample being changed depending on the viscosity of the blood to be examined.

As another example, a plurality of control sample chambers 112 may be provided, and the stirring controller 160 may control the stirrers 121 and 122 in the control sample chambers 112 so that shearing forces having different magnitudes, all sufficient to activate the platelets, are applied to the blood samples in the control sample chambers 112. The stirring controller 160 controls the stirrers 121 and 122 in the standard sample chamber 111 so that a shearing force having a magnitude insufficient to activate the platelets is applied to the blood sample in the standard sample chamber 111.

In the case of the above-described embodiment, the platelet-testing chip 100 according to the embodiment shown in FIG. 4C or 4D may be used. For example, a shearing force of 0.5 Pa or less may be applied to the blood sample in the standard sample chamber 111, and shearing forces of 3 Pa, 5 Pa, and 8 Pa may be applied to the three control sample chambers 112, thus measuring the extent of reaction of the platelets depending on the magnitude of the shearing force. Thereby, the critical shearing force of the current blood sample may be measured.

The reagents 171 applied on the microbeads 170 received in the standard sample chamber 111 and the control sample chamber 112 may be the same as each other so that the extent of reaction of the platelets depending on the shearing force is identified in the blood sample flowing from the standard sample chamber 111 and the control sample chamber 112. As described above, examples of the reagent 171 may include any one among agonists such as collagen, fibrinogen, adenosine diphosphate (ADP), epinephrine, arachidonic acid, thromboxane A2, thrombin, and iso-thrombin-receptor-activating peptide (iso-TRAP), or combinations thereof.

As another example, the stirring controller 160 may apply a shearing force having a magnitude insufficient to activate the platelets, for example, a shearing force of 0.5 Pa or less, to the blood samples in the standard sample chamber 111 and the control sample chamber 112 in the state in which the microbeads 170 are not added to the standard sample chamber 111 but are added only to the control sample chamber 112, thus enabling the blood samples to flow. This makes it possible to identify the extent of reaction of the platelets depending on the type of reagents.

When a plurality of control sample chambers 112 is provided, the microbeads 170 coated with the different reagents 171 may be received in respective control sample chambers 112, thus identifying the extent of reaction of the platelets with respect to each reagent 171.

Meanwhile, the exit chamber 140 is connected to the microchannels 131 and 132 through the respective waste sample chambers 141 and 142. In addition, a vacuum-forming device 300, as will be described later, may be connected through the exit chamber 140 to introduce a vacuum pressure into the exit chamber 140, thus enabling the blood samples in a plurality of sample chambers 111 and 112 to flow into the respective microchannels 131 and 132 due to the vacuum pressure applied through the exit chamber 140.

The exit chamber 140 may be sealed with a rubber stopper 140a at an entrance portion thereof, as shown in FIG. 1, allowing the inflow of the vacuum pressure into the exit chamber 140. When the stopper 140a is formed of a rubber material, the end of the vacuum-forming device 300 may have the shape of a syringe needle, whereby connection to the inside of the exit chamber 140 is made possible using injection of the needle while the stopper 140a covers the exit chamber 140. In addition, the sealing structure of the exit chamber 140 and the connection structure of the exit chamber to the vacuum-forming device 300 may be embodied in various forms other than the above-mentioned examples by those skilled in the art, and it is readily apparent that the technical idea of the present invention is not limited thereto.

The first embodiment of the present invention exemplifies that the exit chamber 140 is connected to the microchannels 131 and 132. This allows the blood samples to simultaneously flow from the sample chambers 111 and 112 through the corresponding microchannels 131 and 132 due to the vacuum pressure applied through one exit chamber 140. Accordingly, the vacuum pressure that induces the flow of the blood samples in the microchannels 131 and 132 is applied to the microchannels 131 and 132 through one exit chamber 140, so that the vacuum pressure applied to the microchannels 131 and 132 is maintained uniform and so that the flows of the blood samples are taken at the same point in time using an image acquisition device such as a camera, whereby it is possible to more accurately test the characteristics of the platelets.

Meanwhile, the platelet-testing chip 100 according to the first embodiment of the present invention may include an entrance chamber 140, as shown in FIGS. 1 and 2.

The entrance chamber 110 is formed so as to be connected to the plurality of sample chambers 111 and 112. Referring to FIG. 3, the upper part of the entrance chamber 110 may be open to the outside so that the blood sample is injected. In addition, the lower part of the entrance chamber 110 communicates with the sample chambers 111 and 112 so that the blood samples injected into the entrance chamber 110 are evenly distributed to the sample chambers 111 and 112.

Meanwhile, the stirrers 121 and 122 according to the first embodiment of the present invention may have the shape of a round straight bar, a tapered round bar with a radius being reduced from the center thereof, a round plate, or a conical plate with a radius being reduced from the center thereof. When the stirring controller 160 applies the shearing force having a magnitude sufficient to activate the platelets, that is, when the stirring controller applies the shearing force to the control sample chamber 112, the stirring time may range from 10 seconds to 300 seconds depending on the shape of the stirrers 121 and 122. For example, when the stirrers 121 and 122 have the shape of a round bar, the stirrers may be rotated for about 180 seconds, thus applying the shearing force to the platelets. On the other hand, when the stirrers 121 and 122 have the shape of a conical plate, the stirrers may be rotated for a very short time of about 10 seconds.

When the stirrers 121 and 122 are rotated by the force obtained using the above-described non-contact method, stirring and shear flow depending on the number of rotations of the stirrers 121 and 122 occur in the sample chambers 111 and 112. As for the shear flow, when the stirrer has the shape of a round straight bar, an intermittent shear flow may occur, and when the stirrer has the shape of a round plate, a continual shear flow may occur. The stirrers 121 and 122 may be made of a metal material which is magnetized by a magnetic force and which is influenced by the magnetic force without mechanical connection.

In addition, preferably, the diameter or the thickness of the stirrers 121 and 122 may be substantially the cutting size of the depth of the sample chambers 111 and 112, and the length or the diameter of the stirrers 121 and 122 may be 80 to 90% of the diameter of the sample chambers 111 and 112.

Referring again to FIGS. 1 and 2, the platelet-testing chip 100 according to the first embodiment of the present invention may include addition chambers 161 and 162 formed between the clogging-induction channel units 151 and 152 and the sample chambers 111 and 112.

Calcium ions may be provided in the addition chambers 161 and 162. The calcium ions promote the activation of the platelets due to the reagent 171 transferred together with the blood samples passing through the addition chambers 161 and 162 or the reagent 171 in the clogging-induction channel units 15 and 152. Accordingly, attachment and aggregation of the platelets may be performed more smoothly.

Further, the first embodiment exemplifies that the microbeads 170 are coated with the reagent for activating the platelets. In addition, in the platelet-testing chip 100 according to the first embodiment of the present invention, the microbeads 170 may be coated with an antagonist reagent.

In addition, the microbeads may be received only in the control sample chamber 112, and one or more of final reaching distances, reaching times required for the final reaching distances, and flow rates of the blood sample that flows from the standard sample chamber 111 to the microchannel 131 and the blood sample that flows from the control sample chamber 112 to the microchannel 132 may be selected, followed by comparison thereof, thus measuring the characteristics of the platelets.

For example, when the degree of response to a drug is measured using the blood sample of a patient taking an antagonist drug, such as a platelet-related drug, for example, an anti-platelet agent, a shearing force having a magnitude insufficient to activate the platelets is applied to the blood samples in the standard sample chamber 111 and the control sample chamber 112, and the microbeads 170 are included only in the control sample chamber 112.

Accordingly, it is possible to identify how the antagonist drug, such as the anti-platelet agent being taken by the patient, acts on the patient, that is, the extent of reaction of the platelets with respect to the drug being taken.

More specifically, when the blood sample of a person having a normal platelet function or a person taking aspirin and clopidogrel is reacted with a reagent such as antagonist adenosine diphosphate (agonist ADP), prosraglandin E, fibrinogen, and arachidonic acid, if the function of the platelets of the subject is normal, the flow path in the microchannels 131 and 132 may be clogged within a short time, which stops the flow or causes a short flow distance. Conversely, if the function of the platelets is abnormal, the clogging time is increased or the transfer distance is increased compared to the normal case.

Therefore, in the case where experiments are performed so that the microbeads 170, that is, the reagent 171, are not included in the standard sample chamber 111 but are included in the control sample chamber 112, it is possible to identify the extent of reaction of the platelets with respect to the drug being taken by, for example, comparing the flow distances to each other, as a result of the two experiments.

An antagonist reagent such as an anti-platelet agent may be an antagonist such as aspirin, a P2Y1 receptor antagonist, and a P2Y12 receptor antagonist. Examples of the P2Y1 receptor antagonist may include at least one of MRS 2179, MRS 2279, MRS 2500, A2P5P, A3P5P, and A3P5PS candidate materials.

Further, examples of the P2Y12 receptor antagonist may include at least one of clopidogrel, ticlopidine, prasugrel, AR-C67085MX, cangrelor, C1330-7, MRS 2395, and 2-methylthioadenosine-5'-monophosphate candidate materials.

Figure 6:
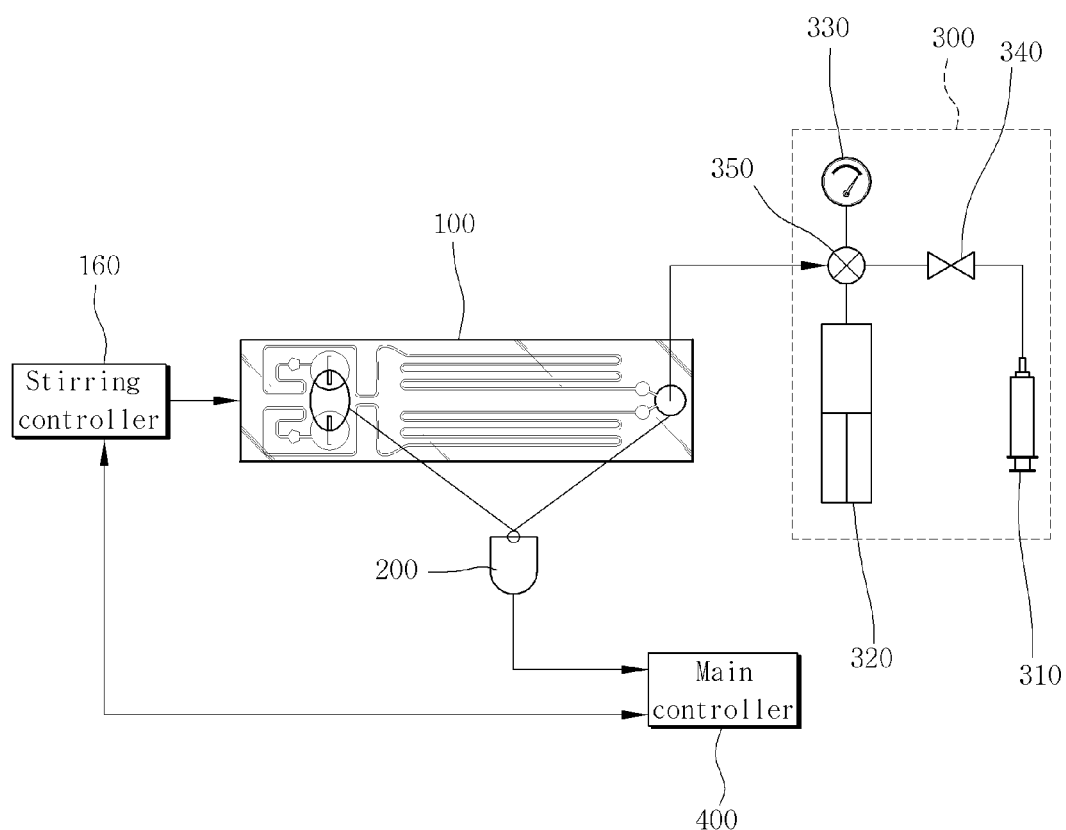
FIG. 6 is a view showing the constitution of a platelet-testing device according to the present invention.

Hereinafter, the configuration of a platelet-testing device using the platelet-testing chip 100 will be described in detail with reference to FIG. 6.

The platelet-testing device according to the present invention includes a platelet-testing chip 100, a vacuum-forming device 300, and a sensing device 200. The flow of the blood sample occurs in the platelet-testing chip 100, and the constitution thereof has been described above. Accordingly, a description thereof will be omitted.

Figure 8:
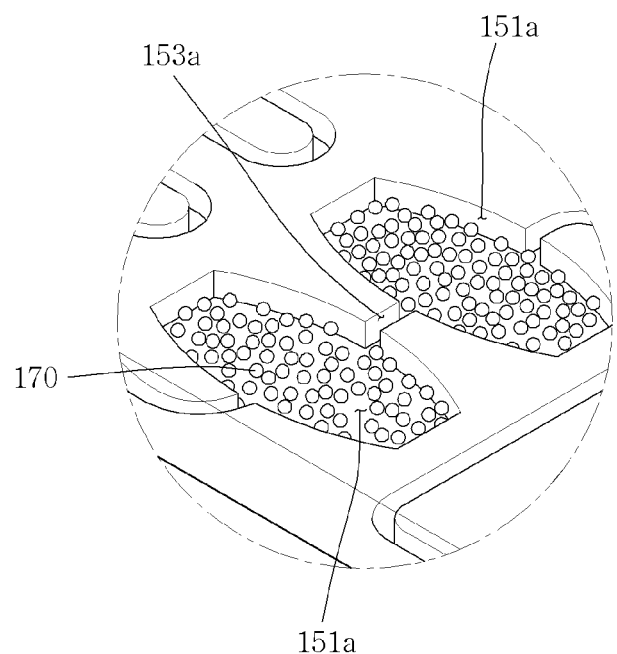
FIG. 8 is an enlarged view of region B in FIG. 7.

The vacuum-forming device 300 serves to apply the vacuum pressure so as to induce the blood sample to flow in the platelet-testing chip 100. The vacuum-forming device 300 according to the present invention may include a vacuum pump 310, a dead volume chamber 320, a pressure measurement sensor 330, and a valve 340, as shown in FIG. 8.

The vacuum pump 310 is connected to the exit chamber 140 to generate the vacuum pressure. As described above, when the exit chamber 140 is closed using the rubber stopper 140a, the end of the vacuum pump 310, that is, the portion connected to the exit chamber 140, may have the shape of a syringe needle and may be inserted into the rubber stopper 140a, thus being connected to the inside of the exit chamber 140. In the present invention, for example, the vacuum pump 310 is provided in a type of a syringe pump.

The dead volume chamber 320 is connected in parallel with the vacuum pump 310 and the exit chamber 140, which maintains a predetermined vacuum pressure on the exit chamber 140. In addition, the valve 340 is provided between the vacuum pump 310 and the exit chamber 140 to control the vacuum pressure applied to the exit chamber 140. In the present invention, for example, a solenoid valve is used as the valve 340. In addition, the vacuum pressure applied to the exit chamber 140 is measured using the pressure measurement sensor 330.

The flow of the blood sample in the platelet-testing chip 100 is sensed using the sensing device 200. In the present invention, for example, the sensing device 200 is provided with an image acquisition device for acquiring an image such as a CCD or a CMOS, or with a reach-sensing device 200 for sensing the blood sample passing through a specific position in the microchannels 131 and 132.

In the case of the image acquisition device, it is possible to measure the final reaching distance, the reaching time required for the final reaching distance, and the flow rate of the blood sample by processing the taken image. The reach-sensing device 200 may be used to measure the reaching time by sensing whether or not the blood sample reaches a specific position of the end of the microchannels 131 and 132. For example, an LED or a photodiode sensor may be used to sense whether or not the blood sample reaches the specific position.

A main controller 400 serves to control the overall function of the platelet-testing device according to the present invention. For example, a signal such as an image transmitted from the sensing device 200 is processed to calculate the reaching distance, the reaching time, and the flow rate and to control the vacuum-forming device 300 such as a syringe pump.

In addition, depending on the experimental conditions, the main controller commands the stirring controller 160 to vary the rotation speed of the stirrers 121 and 122, whereby the stirring controller 160 serves to individually control the stirrers 121 and 122 in the sample chambers 111 and 112.

Accordingly, a process of testing the function of the platelets in blood using the platelet-testing device according to the present invention will be described as an example of an experiment using different shearing forces.

First, the blood of a subject is sampled, and a blood sample is injected into the entrance chamber 110. During the injection, the exit chamber 140 is closed, and the vacuum-forming device 300 is not operated.

The blood samples injected into the entrance chamber 110 are equally distributed to the sample chambers 111 and 112, that is, the standard sample chamber 111 and the control sample chamber 112. In addition, when the distribution of the blood samples to the standard sample chamber 111 and the control sample chamber 112 is finished, the stirring controller 160 enables the stirrers 121 and 122 to rotate. As described above, for example, the rotation speed of the stirrer 121 and 122 in the standard sample chamber 111 is controlled so that a shearing force having a magnitude insufficient to activate the platelets is applied, and the rotation speed of the stirrer 121 and 122 in the control sample chamber 112 is controlled so that a shearing force having a magnitude sufficient to activate the platelets is applied.

When the stirring of the blood samples is finished using the stirring of the stirrers 121 and 122, the valve 340 of the vacuum-forming device 300 is opened, and vacuum pressure is applied to the entrance and exit chambers by the vacuum pump 310. The magnitude of the vacuum pressure applied to the exit chamber 140 may be maintained using the dead volume chamber 320.

When the vacuum pressure is applied through the exit chamber 140, the blood samples received in the standard sample chamber 111 and the control sample chamber 112 flow through the respective microchannels 131 and 132 connected thereto. The blood sample including the activated platelets in the control sample chamber 112 exhibits relatively more frequent attachment or aggregation of the platelets during a flow process than the blood sample in the standard sample chamber 111. In particular, when the blood sample passes through the clogging-induction channel units 151 and 152 and the clogging-induction channels 153 and 154, attachment or aggregation is remarkably frequently exhibited.

When the flow of the blood sample is stopped through the above-described process, the main controller 400 serves to calculate the final reaching distance, the reaching time required for the final reaching distance, and the flow rate of the blood sample based on the image during the flow process obtained using the sensing device 200, for example, the image acquisition device. The results of the standard sample chamber 111 and the control sample chamber 112 are compared to each other, thereby measuring the extent of shear-induced activation of the blood sample and the extent of aggregation or attachment of the platelets.

For example, a percentage platelet aggregation (PA), among the characteristics of the platelets, may be calculated using any one among the following equations: $PA=(Lc/Lr)\times 100$, $PA=(Vc/Vr)\times 100$, and $PA=(Tr/Tc)\times 100$. Lc, Tc, and Vc are respectively the final reaching distance, the reaching time required for the final reaching distance, and the flow rate of the blood sample flowing from the control sample chamber 112 to the corresponding microchannel 132. Lr, Tr, and Vr are respectively the final reaching distance, the reaching time required for the final reaching distance, and the flow rate of the blood sample flowing from the standard sample chamber 111 to the corresponding microchannel 131.

In addition, a percentage platelet inhibition (PI), among the characteristics of the platelets, may be calculated using any one among the following equations: $PI=(1-(Lc/Lr))\times 100$, $PI=(1-(Vc/Vr))\times 100$, and $PI=(1-(Tr/Tc))\times 100$. That is, the percentage platelet inhibition may be calculated using the equation: percentage platelet inhibition $(PI)=1-$percentage platelet aggregation (PA).

Figure 7:
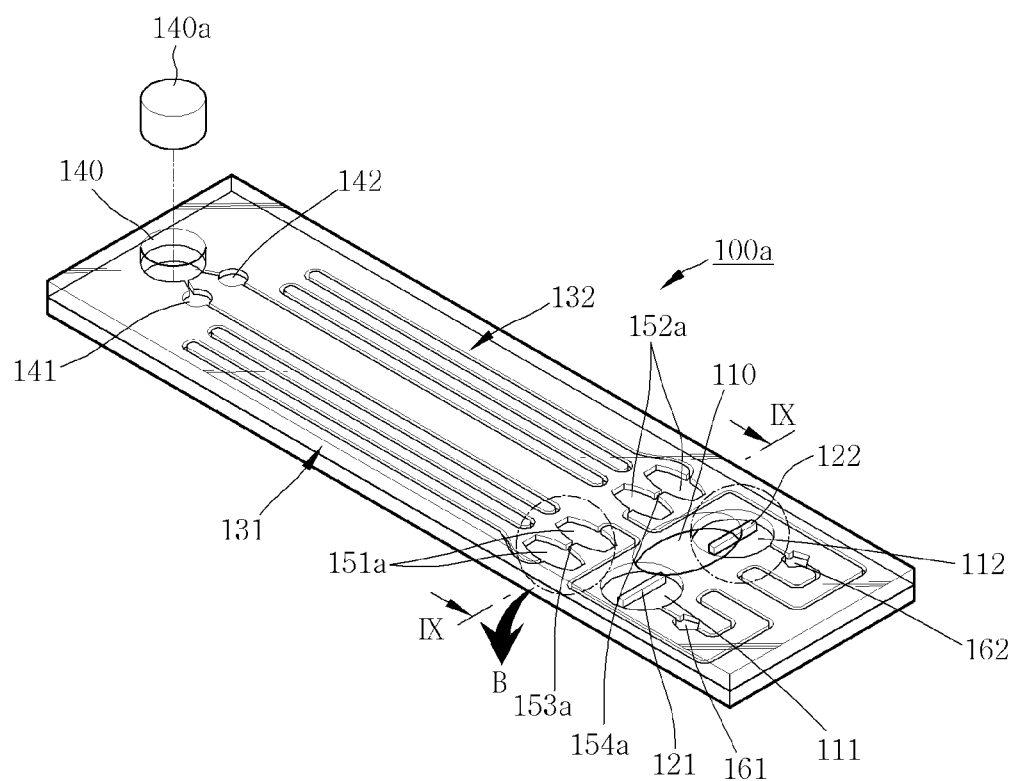
FIG. 7 is a perspective view of a platelet-testing chip according to a second embodiment of the present invention.
Figure 9:
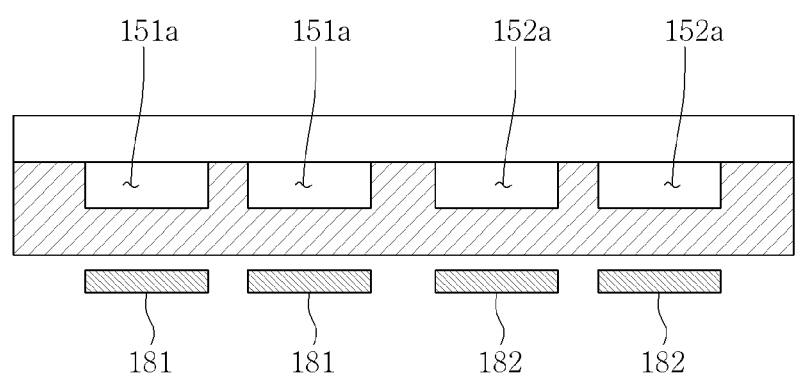
FIG. 9 is a cross-sectional view taken along the line IX-IX in FIG. 7.

Hereinafter, a platelet-testing chip 100a according to a second embodiment of the present invention will be described with reference to FIGS. 7 to 9. The platelet-testing chip 100 according to the second embodiment of the present invention will be described with an emphasis on the constitution thereof that is different from that of the first embodiment.

In the platelet-testing chip 100a according to the second embodiment of the present invention, the microbeads 170 coated with the reagent 171 may not be received in the sample chambers 111 and 112, but may be received in at least one of the clogging-induction channel units 151a and 152a as shown in FIG. 8.

The clogging-induction channel units 151a and 152a according to the second embodiment of the present invention have a diameter that is larger than the inner diameter of the microchannels 131 and 132. FIG. 7 exemplifies that two clogging-induction channel units 151*a* and 152*a* are formed in one microchannel, that the clogging-induction channel units 151*a* are connected through a clogging-induction channel 153*a*, and that the clogging-induction channel units 152*a* are connected via clogging-induction channels 154*a*.

In addition, magnetic units 181 and 182 serve to apply a magnetic field to the inside of the clogging-induction channel units 151*a* and 152*a*, and the microbeads 170 include a material having magnetism or a magnetizable material.

Accordingly, the microbeads 170 are received in the clogging-induction channel units 151*a* and 152*a* due to the magnetism of the magnetic units 181 and 182, thus activating the platelets of the blood sample passing through the clogging-induction channel units 151*a* and 152*a* due to the applied reagent 171. Thereby, attachment and aggregation between the microbeads 170 and the platelets are induced, and the microbeads 170 are captured in the clogging-induction channel units 151*a* and 152*a* due to the magnetic field of the magnetic units 181 and 182, which induces clogging with the blood sample.

It is readily apparent that the measurement examples of the first embodiment, applied when the microbeads 170 are received in the sample chambers 111 and 112, can also be applied to the case where the microbeads 170 are received in the clogging-induction channel units 151 and 152. The constitutions applied to the standard sample chamber 111 and the control sample chamber 112 are respectively applied to a standard clogging-induction channel unit 151*a* connected to the standard sample chamber 111 and a control clogging-induction channel unit 152*a* connected to the control sample chamber 112.

The first embodiment exemplifies that the clogging-induction channel units 151 and 152 have an inner diameter smaller than that of the microchannels 131 and 132 or that the inner side thereof includes a material for activating the platelets. In addition, as in the second embodiment, the microbeads 170 include a material having magnetism or a magnetizable material, and the magnetic units 181 and 182 serve to apply a magnetic field to the clogging-induction channel units 151 and 152. Thereby, the microbeads 170 are captured in the clogging-induction channel units 151 and 152 due to the magnetic field of the magnetic unit, which induces aggregation and attachment of the platelets in the state in which the flow of the blood samples is impeded or stopped, thus clogging the clogging-induction channel units 151 and 152.

Further, the above-described embodiments exemplify that the microbeads 170 have a spherical shape. In addition, the microbeads 170 may have a plurality of pores through which an inner part communicates with an outer part. That is, the microbeads 170 may be porous.

The reagent 171 may be applied to flow into the pore, so that when the reagent 171 flows together with the blood sample, the reagent 171 on the outer surface of the microbead is first dissolved and reacts with the platelets and so that the reagent flows out from the pore while being dissolved during the flow process and continuously reacts with the platelets.

This embodiment is intended to clarify a part of the technical idea included in the present invention, and it is obvious that modifications and specific embodiments which can be easily devised by those skilled in the art are included in the technical idea of the present invention within the scope of the technical idea included in the specification of the present invention.

<Description of Reference Numerals in the Drawings>

| | |
|---|---|
| 100, 100a: Platelet-testing chip | 110: Entrance chamber |
| 111, 112: Standard sample chamber | 121, 122: Stirrer |
| 131, 132: Microchannel | 140: Exit chamber |
| 141, 142: Waste sample chamber | 151, 152: Clogging-induction channel unit |
| 153a, 154a: Clogging-induction channel | 160: Stirring controller |
| 161, 162: Addition chamber | 170: Microbead |
| 171: Specimen | 181, 182: Magnetic unit |
| 200: Sensing device | 300: Vacuum-forming device |
| 310: Vacuum pump | 320: Dead volume chamber |
| 330: Pressure measurement sensor | 340: Valve |
| 400: Main controller | |

INDUSTRIAL APPLICABILITY

The present invention is applied to the field of platelet function testing.

The invention claimed is:

1. A platelet-testing chip comprising:
a plurality of sample chambers storing blood samples;
stirrers provided in the sample chambers, respectively, to stir the blood samples;
a plurality of waste sample chambers provided so as to correspond to the plurality of the sample chambers;
microchannels, through which the sample chambers and the waste sample chambers corresponding to each other are independently connected to thus form paths through which the blood samples flow from the sample chambers to the corresponding waste sample chambers;
clogging-induction channel units formed on the paths of the microchannels;
addition chambers formed between the clogging-induction channel units and the plurality of sample chambers and comprising calcium ions or adenosine diphosphates (ADP);
microbeads which are received in one or more of the plurality of the sample chambers and which are coated with a reagent for activating platelets on an outer surface thereof; and
magnetic units applying a magnetic field to the clogging-induction channel units,
wherein when the blood samples are transferred from the sample chambers through the microchannels, the microbeads are transferred together with the blood samples, thus inducing clogging of the clogging-induction channel units with the blood samples,
wherein the platelets of the blood samples are attached to the microbeads and are aggregated in the sample chambers and the microchannels, and then flow into the clogging-induction channel units, thus clogging the clogging-induction channel units, and
wherein the microbeads include a material having magnetism or a magnetizable material so as to be captured in the clogging-induction channel units due to the magnetism of the magnetic units while flowing together with the blood samples, thus impeding or stopping a flow of the blood samples.

2. The platelet-testing chip of claim 1, wherein a reagent for activating the platelets is applied on inner wall surfaces of the clogging-induction channel units to induce clogging.

3. The platelet-testing chip of claim 2, wherein the reagent applied on the inner wall surfaces of the clogging-induction channel units is an antagonist comprising at least one of collagen, fibrinogen, adenosine diphosphate (ADP), epinephrine, arachidonic acid, thromboxane A2, thrombin, and iso-thrombin-receptor-activating peptide (iso-TRAP), or a combination thereof.

4. The platelet-testing chip of claim 1, wherein inner diameters of the clogging-induction channel units are smaller than inner diameters of the microchannels so as to induce clogging.

5. The platelet-testing chip of claim 1, wherein the reagent applied on the microbeads is an antagonist comprising at least one of collagen, fibrinogen, adenosine diphosphate (ADP), epinephrine, arachidonic acid, thromboxane A2, thrombin, and iso-thrombin-receptor-activating peptide (iso-TRAP), or a combination thereof.

6. The platelet-testing chip of claim 1, wherein the plurality of the sample chambers includes a standard sample chamber and one or more control sample chambers, and one or more of final reaching distances, reaching times required for the final reaching distances, and flow rates of the blood samples that flow from the standard sample chamber to the corresponding microchannel and of the blood samples that flow from the control sample chambers to the corresponding microchannels are selected, followed by comparison thereof, thus measuring characteristics of the platelets.

7. The platelet-testing chip of claim 6, further comprising:
a stirring controller individually controlling the stirrers provided in the sample chambers so that magnitudes of shearing forces applied to the blood samples in the sample chambers are individually controlled.

8. The platelet-testing chip of claim 7, wherein the stirring controller controls the stirrers in standard sample chambers so that the shearing forces having the magnitudes insufficient to activate platelets are applied to the blood samples in the standard sample chambers, and also controls the stirrers in the control sample chambers so that the shearing forces having the magnitudes sufficient to activate the platelets are applied to the blood samples in the control sample chambers, and microbeads received in the standard sample chambers and the control sample chambers are coated with a same reagent so that an extent of reaction of the platelets depending on the shearing forces is identified.

9. The platelet-testing chip of claim 7, wherein the control sample chambers are provided in a plural number, the stirring controller controls the stirrers in standard sample chambers so that the shearing forces having the magnitudes insufficient to activate the platelets are applied to the blood samples in the standard sample chambers, and also controls the stirrers in the control sample chambers so that the shearing forces having the different magnitudes sufficient to activate the platelets are applied to the blood samples in the control sample chambers in order to determine an extent of activation of the platelets depending on the magnitudes of the shearing forces, and microbeads received in the standard sample chambers and the control sample chambers are coated with a same reagent so that an extent of reaction of the platelets depending on the shearing forces is identified.

10. The platelet-testing chip of claim 7, wherein the control sample chambers are provided in a plural number, the microbeads are received only in the control sample chambers, the microbeads received in the control sample chambers are coated with different reagents, and the stirring controller applies the shearing forces having the magnitudes insufficient to activate the platelets to the blood samples in standard sample chambers and the control sample chambers.

11. The platelet-testing chip of claim 1,
wherein the calcium ions or the adenosine diphosphates (ADP) are transferred together with the blood samples passing through the addition chambers, thus promoting activation of the platelets using a reagent.

* * * * *